United States Patent [19]
Porter

[11] Patent Number: 6,035,715
[45] Date of Patent: Mar. 14, 2000

[54] METHOD AND APPARATUS FOR OPTIMIZING THE DESIGN OF A PRODUCT

[75] Inventor: Alexander J. Porter, Kalamazoo, Mich.

[73] Assignee: Entela, Inc,, Grand Rapids, Mich.

[21] Appl. No.: 08/929,839

[22] Filed: Sep. 15, 1997

[51] Int. Cl.⁷ ............................ G01M 7/06; G01N 17/02; G01N 17/00

[52] U.S. Cl. .............................. 73/571; 73/663; 73/865.6; 73/432.1

[58] Field of Search ............................... 73/662, 663, 664, 73/665, 666, 667, 668, 865.6, 865.9, 866, 432.1, 672, 571, 573, 574

[56] References Cited

U.S. PATENT DOCUMENTS

| | | | |
|---|---|---|---|
| 2,850,893 | 9/1958 | Barnes, Jr. | 73/665 |
| 3,592,041 | 7/1971 | Spencer | 73/7 |
| 3,597,960 | 8/1971 | Otera et al. | 73/12.04 |
| 3,628,378 | 12/1971 | Regan, Jr. | 73/798 |
| 3,646,807 | 3/1972 | Gray et al. | 73/665 |
| 3,664,181 | 5/1972 | Conrad et al. | 73/865.6 |
| 3,712,125 | 1/1973 | Meyer | 73/782 |
| 3,732,380 | 5/1973 | Kimball | 360/72.1 |
| 3,942,362 | 3/1976 | Keller | 73/816 |
| 4,069,706 | 1/1978 | Marshall et al. | 73/666 |
| 4,112,776 | 9/1978 | Ouellette et al. | 73/665 |
| 4,181,026 | 1/1980 | Abstein, Jr. et al. | 73/665 |
| 4,181,027 | 1/1980 | Talbott, Jr. | 73/665 |
| 4,181,028 | 1/1980 | Talbott, Jr. | 73/665 |
| 4,263,809 | 4/1981 | Petersen et al. | 73/798 |
| 4,428,238 | 1/1984 | Tauscher | 73/663 |
| 4,445,381 | 5/1984 | Russenberger | 73/666 |
| 4,489,612 | 12/1984 | Griggs | 73/663 |
| 4,537,077 | 8/1985 | Clark et al. | 73/665 |
| 4,635,764 | 1/1987 | Woyski et al. | 188/268 |
| 4,641,050 | 2/1987 | Emerson et al. | 310/27 |
| 4,658,656 | 4/1987 | Haeg | 73/669 |
| 4,700,148 | 10/1987 | Pauly | 331/154 |

(List continued on next page.)

OTHER PUBLICATIONS

Minor, Edward O., "Accelerated Quality Maturity for Avionics", *1996 Proceedings Accelerated Reliability Technology Symposium*—Denver, Colorado, Sep. 16–20, 1996, pp. 1–18.

Haibel, Chet., "Design Defect Tracking", *1996 Proceedings—Accelerated Reliability Technology Symposium*—Denver, Colorado, Sep. 16–20, 1996, pp. 1–12.

Edison, Larry., "Combining Team Spirit and Statistical Tools With the H.A.L.T. Process", *1996 Proceedings—Accelerated Reliability Technology Symposium*—Denver, Colorado, Sep. 16–20, 1996, pp. 1–8.

Stewart, Ph.D., P.E., Bret A. "Fault Coverage and Diagnostic Efficiency Related to Accelerated Life Testing", *1996 Proceedings—Accelerated Reliability Technology Symposium*—Denver, Colorado, Sep. 16–20, 1996, pp. 1–5.

Granlund, Kevin, "A Method of Reliability Improvement Using Accelerated Testing Methodologies", *1996 Proceedings—Accelerated Reliability Technology Symposium*—Denver, Colorado, Sep. 16–20, 1996, pp. 1–9.

Morelli, Mark L., & Masotti, Robert V., "History of Accelerated Reliability Testing at Otis Elevator Company", *1996 Proceedings—Accelerated Reliability Technology Symposium*—Denver, Colorado, Sep. 16–20, 1996, pp. 1–8.

Cooper, Michael R., "Statistical/Numerical Methods for Stress Screen Development", *1996 Proceedings—Accelerated Reliability Technology Symposium*—Denver, Colorado, Sep. 16–20, 1996, pp 1–37.

(List continued on next page.)

*Primary Examiner*—Hezron Williams
*Assistant Examiner*—Rose M. Miller
*Attorney, Agent, or Firm*—Harness, Dickey & Pierce, P.L.C.

[57] ABSTRACT

A method and apparatus is described for optimizing the design of products, such as but not limited to mechanical products, by simultaneously subjecting the products to multiple stimuli, such as but not limited to temperature, vibration, pressure, ultraviolet radiation, chemical exposure, humidity, mechanical cycling, and mechanical loading.

125 Claims, 4 Drawing Sheets

U.S. PATENT DOCUMENTS

| | | | |
|---|---|---|---|
| 4,715,229 | 12/1987 | Butts | 73/663 |
| 4,733,151 | 3/1988 | Butts | 318/645 |
| 4,735,089 | 4/1988 | Baker et al. | 73/663 |
| 4,802,365 | 2/1989 | Sallberg et al. | 73/808 |
| 4,862,737 | 9/1989 | Langer | 73/117 |
| 4,869,111 | 9/1989 | Ohya et al. | 73/811 |
| 4,912,980 | 4/1990 | Baughn | 73/663 |
| 4,977,342 | 12/1990 | Adams | 310/20 |
| 4,996,881 | 3/1991 | Tauscher et al. | 73/665 |
| 5,038,617 | 8/1991 | Rollet et al. | 73/662 |
| 5,079,955 | 1/1992 | Eberhardt | 73/799 |
| 5,138,884 | 8/1992 | Bonavia | 73/662 |
| 5,154,567 | 10/1992 | Baker et al. | 73/665 |
| 5,156,051 | 10/1992 | Marshall | 73/663 |
| 5,197,333 | 3/1993 | Garcia-Gardea | 73/666 |
| 5,305,645 | 4/1994 | Reifsnider et al. | 73/808 |
| 5,315,882 | 5/1994 | Meyer et al. | 73/862.044 |
| 5,339,677 | 8/1994 | Haug | 73/49.5 |
| 5,339,697 | 8/1994 | Mullin | 73/862.043 |
| 5,343,752 | 9/1994 | Woyski et al. | 73/665 |
| 5,351,545 | 10/1994 | Lucas | 73/663 |
| 5,353,654 | 10/1994 | Lin | 73/865.9 |
| 5,375,453 | 12/1994 | Rudd et al. | 73/865.6 |
| 5,379,645 | 1/1995 | Smart | 73/794 |
| 5,386,728 | 2/1995 | Norton et al. | 73/668 |
| 5,425,276 | 6/1995 | Gram et al. | 73/816 |
| 5,431,491 | 7/1995 | Melgaard et al. | 312/232.1 |
| 5,437,191 | 8/1995 | Dripke et al. | 73/816 |
| 5,476,009 | 12/1995 | Dimarogonas | 73/582 |
| 5,487,301 | 1/1996 | Muller et al. | 73/118.1 |
| 5,544,478 | 8/1996 | Shu et al. | 60/39.03 |
| 5,544,528 | 8/1996 | Woyski et al. | 73/665 |
| 5,553,501 | 9/1996 | Gaddis et al. | 73/662 |
| 5,574,226 | 11/1996 | Reuther et al. | 73/669 |
| 5,594,177 | 1/1997 | Hanse | 73/663 |
| 5,610,334 | 3/1997 | Ueda et al. | 73/865.6 |
| 5,641,912 | 6/1997 | Manahan, Sr. | 73/797 |
| 5,652,386 | 7/1997 | Dimarogonas | 73/582 |
| 5,665,919 | 9/1997 | Woyski et al. | 73/665 |
| 5,675,098 | 10/1997 | Hobbs | 73/865.6 |
| 5,700,951 | 12/1997 | Sagiyama et al. | 73/11.08 |
| 5,715,180 | 2/1998 | Hu | 364/552 |
| 5,744,724 | 4/1998 | Hobbs | 73/665 |
| 5,752,834 | 5/1998 | Ling | 434/58 |
| 5,813,541 | 9/1998 | Mottram | 209/2 |
| 5,836,202 | 11/1998 | Hobbs | 73/665 |

OTHER PUBLICATIONS

Blemel, Kenneth G., "Virtual HALT and HASS Planning for Stress Testing From Architecture Selection Through Design" *1996 Proceedings—Accelerated Reliability Technology Symposium*—Denver, Colorado, Sep. 16–20, 1996, pp. 1–6.

Moss, Dick, "The Myth of Burn–in" *1996 Proceedings—Accelerated Reliability Technology Symposium*—Denver, Colorado, Sep. 16–20, 1996, pp. 1–4.

Hobbs, Gregg K., "Reliability—Past and Present", *1996 Proceedings—Accelerated Reliability Technology Symposium*—Denver, Colorado, Sep. 16–20, 1996, pp. 1–5.

O'Connor, Patrick D.T., "Achieving World Class Quality & Reliability: Science or Art?", *1996 Proceedings—Accelerated Reliability Technology Symposium*—Denver, Colorado, Sep. 16–20, 1996, pp. 1–4.

McLinn, James A. "Constant Failure Rate—A Paradigm In Transition?", *Quality and Reliability Engineering International*, vol. 6, pp. 237–241 (1990).

Leonard, Charles T., et al., "How Failure Prediction Methodology Affects Electronic Equipment Design", *Quality and Reliability Engineering International*, vol. 6, pp. 243–249 (1990).

Wong, Kam L., "What is Wrong With The Existing Reliability Prediction Methods", *Quality and Reliability Engineering International*, vol. 6, pp. 251–257 (1990).

Blanks, Henry S., "Arrhenius And The Temperature Dependence Of Non–Constant Failure Rate", *Quality and Reliability Engineering International*, vol. 6, pp. 259–265 (1990).

Pecht, Michael, et al., "The Reliability Physics Approach To Failure Prediction Modelling", *Quality and Reliability Engineering International*, vol. 6, pp. 267–273 (1990).

Pecht, Michael et al., "Temperature Dependence of Microelectronic Device Failures", *Quality and Reliability Engineering International*, vol. 6, pp. 275–284 (1990).

Ganter, William A., "Increasing Importance of Effects of Marginal Parts On Reliability", *Quality and Reliability Engineering International*, vol. 6, pp. 285–288 (1990).

Beasley, Keith, "New Standards For Old", *Quality and Reliability Engineering International*, vol. 6, pp. 289–294 (1990).

Coppola, Anthony, "A Better Method For Verifying Production Reliability", *Quality and Reliability Engineering International*, vol. 6, pp. 295–299 (1990).

Gregg G. Hobbs, "What HALT and HASS Can Do For Your Product", EE–Evaluation Engineering, Nov. 1997, pp. 138–142.

Edward B. Hakim, "Microelectronic Reliability/Temperature Independence", *Quality and Reliability Engineering International*, 1991, vol. 7, pp. 215–220.

Stephen A. Smithson, "Effectiveness and Economics", *Proceedings of the IES*, 1990, pp. 737–742.

Ronald G. Lambert, "Case Histories of Selection Criteria For Random Vibration Screening", *Journal of Environmental Sciences*, Jan./Feb. 1985, pp. 19–25.

METHOD AND APPARATUS FOR OPTIMIZING THE DESIGN OF A PRODUCT

FIELD OF THE INVENTION

The present invention relates to a new and improved method and apparatus for optimizing the design of products by simultaneously subjecting the products to varying levels of multiple stimuli.

BACKGROUND OF THE INVENTION

One of the major concerns of manufacturers is the discovery of latent defects or flaws which may eventually lead to failure of a product, component or subcomponent. For this reason, manufacturers have employed various testing procedures that expose a mechanical product, component, or subcomponent to various stresses that would normally be expected to contribute to any number of possible failure modes. Once the failure modes were identified, the manufacturers could then redesign the products in order to reduce or even eliminate the failure modes. Some examples of stresses are pressure, ultraviolet radiation, chemical exposure, vibration, temperature (e.g., extreme heat or extreme cold, and rapid changes in temperature), humidity, mechanical cycling (e.g., repeatedly opening and closing a hinged door), and mechanical loading. It should be noted that the terms "product," "component," and "subcomponent," are being used interchangeably throughout the instant application.

Previously, laboratories typically conducted standard testing of mechanical products and components using traditional success based testing. This meant that the goal of the test was to measure the number of products or components that successfully survived a specified number of cycles with a specified stress source level (e.g., vibration, cycle load, temperature, humidity). This testing was generally based on field data and manufacturing/design experience.

Another testing approach was based on the introduction of all the stress sources at service levels to an entire system to provide the final verification test before production. This approach was intended to be a recreation of exact stresses seen on a system during field conditions. For example, an automobile cooling system would receive road vibration, glycol flow, pressure, heat, and ambient conditions just as would be expected to occur during a standard test track durability test.

Therefore, there is a need for a method and apparatus which is capable of generating all possible stress patterns in mechanical products and components under varying simultaneous stimuli in order to activate failure modes.

Testing in accordance with the present invention can lead to significant product quality improvements, design cost reductions, production cost reductions, reduced warranty repair expense, increased customer satisfaction, and increased market share.

SUMMARY OF THE INVENTION

General objects of the present invention are to facilitate and enhance testing of products under various conditions, to provide more comprehensive testing and to make testing more efficient by reducing the energy, time, and expense required to undertake testing.

One aspect of the present invention is to allow products to be more comprehensively tested under multiple stimuli including, but not limited to, temperature, vibration, pressure, ultraviolet radiation, chemical exposure, humidity, mechanical cycling, and mechanical loading. In accordance with this aspect of the present invention, the apparatus and method of the present invention allows products to be tested under varying simultaneous multiple stimuli including, but not limited to, vibration, temperature, pressure, ultraviolet radiation, chemical exposure, humidity, mechanical cycling, and mechanical loading, in order to identify the failure modes of the products.

In accordance with another aspect of the present invention, products are exposed to stimuli that produce uniform random stress patterns in the product.

In accordance with another aspect of the present invention, products are exposed to stimuli that produce six axis uniform random stress patterns in the product.

In accordance with other aspects of the present invention, products may be exposed to varying levels of stimuli. Further, these stimuli may be applied simultaneously to the products. Finally, the level of these simultaneous stimuli may be varied during the course of being applied to the products.

A more complete appreciation of the present invention and its scope can be obtained from understanding the accompanying drawings, which are briefly summarized below, the followed detailed description of the invention, and the appended claims.

DETAILED DESCRIPTION OF THE INVENTION

Figure 1:
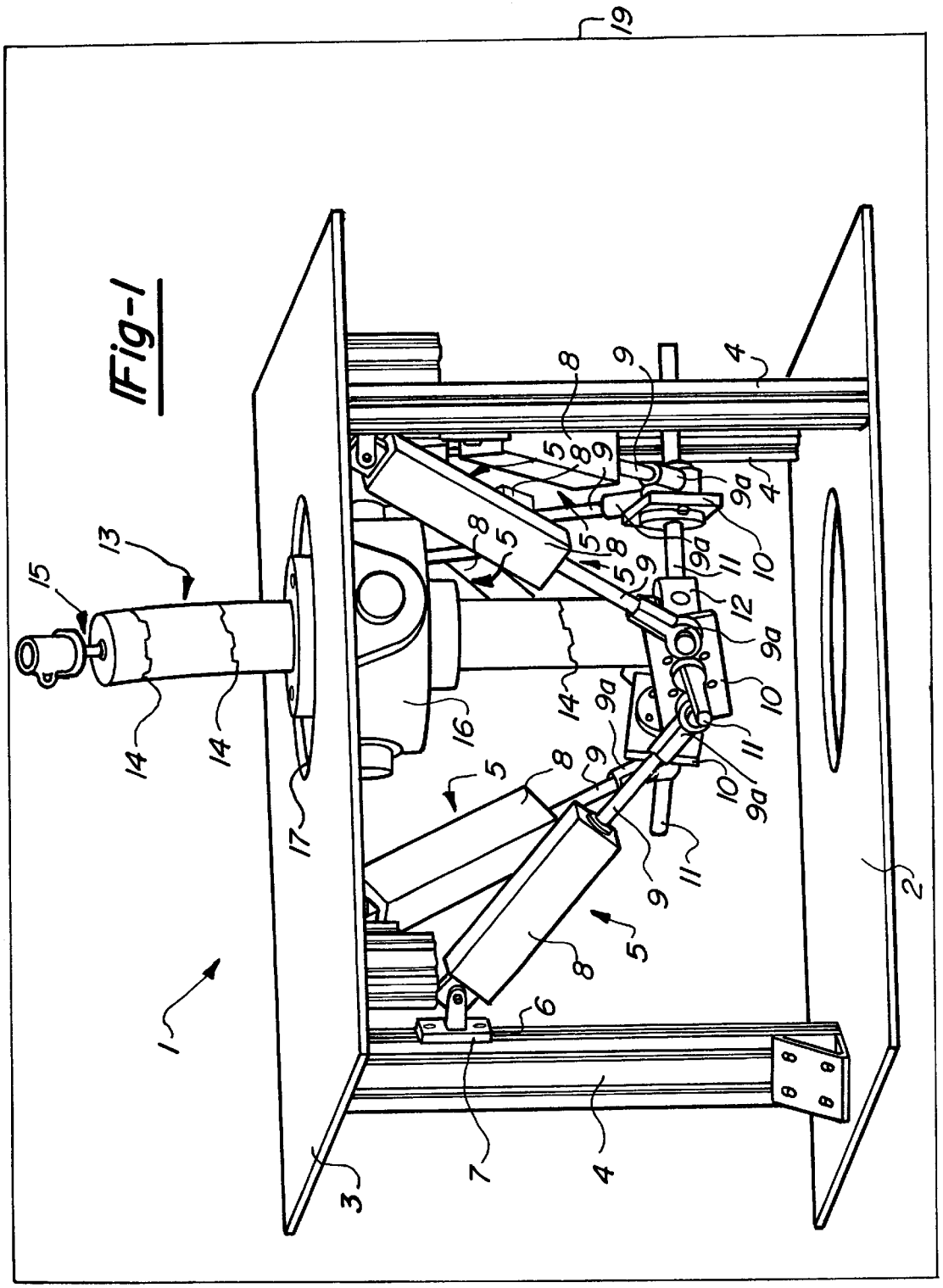
FIG. 1 is a perspective view of an apparatus for testing a product under different conditions, in accordance with one aspect of the present invention.

Generally, mechanical systems typically have resonance frequencies below 200 Hz. Accordingly, a mechanical system (e.g., product, component, subcomponent) may be broadly defined as a system that has at least one mode shape at a frequency below 200 Hz. Conversely, a solid state system typically has a first resonant frequency (also defined as the first mode shape) above 200 Hz.

One of the primary objects of the present invention is to develop a method and apparatus for creating a wide variety of stress patterns, especially six axis uniform random stress patterns, in a product, component, or subcomponent in order to activate the failure modes of that particular product, component, or subcomponent. A six axis uniform random stress is generally defined as the stress history at a point having uniform random distribution with the stress being comprised of tension and compression stress in three orthogonal axes and torsion stress about the same three orthogonal axes. Six axis uniform random stress patterns are generally defined as six axis uniform random stress at all points on a product such that the stress history of the six axis uniform random stress at each point forms a time history of non-repeating stress patterns. All possible stress patterns have an equal probability at any time.

Although the primary focus of the present invention is mechanical products, components, and subcomponents, it should be appreciated that the present invention can be practiced on other types of products, components, and subcomponents such as solid state electronics, brackets, clamps, fasteners, decorative attachments, and many other products which do not meet the definition of a mechanical system.

In a preferred embodiment, it has been found that the use of six axis uniform random actuation at one or more mounting locations of a product will produce six axis uniform random stress patterns in the product. These six axis uniform random stress patterns will identify failure modes previously uncovered with other testing methodologies. Furthermore, the simultaneous introduction of other stimuli (at varying levels), such as temperature, vibration, pressure, ultraviolet radiation, chemical exposure, humidity, mechanical cycling, and mechanical loading, will identify other failure modes associated with the product.

The use of less than six axis actuation (either of input directly to mounting locations of the product or through the use of a rigid table that is activated to six axis motion by some means) will result in less than all of the possible stress patterns being developed and included in the random stress time history of the product. The lack of these stress patterns in the time history of the product has the potential of failing to activate a failure mode in the design of the product. Additionally, the use of three, four, five, or six axis motion in which one or more of the axis motions are dependent on one or more of the other axes will result in certain stress patterns being generated repeatedly with the loss of other stress patterns. Both of these situations have the potential of failing to produce the stress patterns necessary to activate a failure mode which will therefore go undetected until these stress patterns are encountered in field service.

Referring now to FIG. 1, there is shown a perspective view of an apparatus 1 for testing a product under different conditions in accordance with one aspect of the present invention. Although only one device is shown, it should be appreciated that the use of multiple devices to test a product is envisioned. The basic frame of the apparatus 1 consists primarily of a base 2, a planar member 3, and a plurality of support members 4 that rigidly attach the base 2 to the planar member 3.

The base 2 can be constructed of any suitable material provided that it is substantially flat, durable and of sufficient mass to prevent unintended movement of the apparatus 1 during routine operation. Similarly, the planar member 3 can be constructed of any suitable material. The planar member 3 should preferably be substantially flat in order to provide a flush surface for the top edges of the plurality of support members 4. Although only three support members are shown in the drawing, it should be noted that the use of less than or more than three support members is also envisioned.

The plurality of support members 4 serve two primary purposes. First, the plurality of support members 4 rigidly connect the base 2 to the planar member 3. Second, the plurality of support members 4 provide a means to attach a plurality of actuators 5 (some actuators may not be fully depicted due to the orientation of the FIG. 1). The actuators 5 are also referred to as force imparting means. The actuators 5 may be operated either pneumatically, hydraulically, or by a combination of both pneumatic and hydraulic power. Although six actuators are shown in the drawing, it should be noted that the use of less than six actuators is also envisioned. The plurality of actuators 5 may be attached to the plurality of support members 4 in any number of suitable ways. However, it is preferable for the plurality of actuators 5 to be slidably attached to the plurality of support members 4 in order to allow the plurality of actuators 5 a certain degree of freedom of movement. For example, the plurality of support members 4 can be adapted to contain a recess 6 extending vertically along its length. The plurality of actuators 5 could be fitted with an attachment means 7 which could contain an appendage which is loosely received within the recess 6. Additionally, the attachment means 7 could then be rigidly fastened to the plurality of support members 4 to keep the plurality of actuators 5 in place.

If six actuators 5 are being used, they should preferably be arranged in pairs, each pair being set 120 degrees apart from the other pair. Each actuator 5 is simply comprised of a cylinder 8 (some cylinders may not be fully depicted due to the orientation of the figures) acting in cooperation with a piston 9 (some pistons may not be fully depicted due to the orientation of the figures) in order to produce force and torque upon a point of rotation. The pressure to each actuator 5 will be cycled between maximum extend pressure and maximum retract pressure in a linear "saw-tooth" manner. The frequency for each actuator 5 will be slightly different. This difference in frequency will cause an interference pattern of the cycling as the actuators 5 come in and out of phase with each other. It is this difference in the frequencies of the actuators which creates a six axis uniform random stress in the product. As an example, the six pneumatic actuators 5 may be operated at frequencies of 1.8 Hz, 1.9 Hz, 2.0 Hz, 2.1 Hz, 2.2 Hz, 2.3 Hz, and 2.4 Hz, respectively.

Therefore, as the actuators 5 come in and out of phase with one another, the frequency content in the center will go from 2 Hz to infinity. It should be noted that other frequencies may be used for the individual actuators 5 in order to produce an even lower frequency.

The piston portion of each actuator 5 is rotatably fastened to a universal joint 9a, which is in turn rotatably fastened to a slide 10, which is in turn rotatably attached to an attachment means 11 that extends outwardly from a central hub 12. It should be noted that there are a plurality of attachment means 11, which generally correspond in number to the number of slides 10. It should also be noted that each pair of universal joints 9a is attached to its own individual slide 10. The attachment means 11 can comprise any number of suitable means or devices such as rods, bolts, nuts and lock washers, metallurgical attachment (welding), hyper-elastic or semi-elastic restraint, mechanical spring, or ball and socket.

As the actuators 5 are actuated, they produce a force upon the universal joint 9a, which is then transferred from the universal joint 9a to the slide 10, which is then transferred from the slide 10 to the attachment means 11, which is then transferred from the attachment means 11 to the central hub 12, which at that point may generate a torque. It should be noted that whether a torque is generated about the central hub 12 will depend upon which actuators are being actuated and in what sequence with respect to one another.

The central hub 12 represents the lower portion of the force transfer member or force transfer means 13. The primary purpose of the force transfer means 13 is to transfer the force and torque originally created by the plurality of actuators 5 at the central hub 12 to the product itself. Any number of suitable devices can be employed as the force transfer means 13, such as an omni-directional lever or a rod. It should be noted that the force transfer means 13 has a plurality of integral hinge means 14 located at various positions. These integral hinge means 14 allow the force transfer means 13 to be angularly positioned in order to facilitate mounting to the product. In a preferred embodiment, the angular positions are achieved by the geometry of the individual rod sections of the force transfer means 13. Preferably, the rod sections are cut at an angle (e.g., 30 degrees) and the cut surface is provided with an interlocking geometric pattern that is radially symmetric such that two rod sections can be assembled in a multitude of orientations ranging from being coaxially aligned to having their centerlines at some maximum angle. Once the rod sections are positioned in the desired orientation, a cable or chain running the length of the rod sections is tightened by means of a draw down clamp, hydraulic force, or some other force means located in the central hub 12. The purpose of the adjustable orientation of the rod sections is to allow the free rod end (i.e., the portion of the force transfer means containing the mounting means) to be positioned in an orientation that is most advantageous to mounting the apparatus to a mounting location or some other point of the product to be tested. Other means and devices which are envisioned to essentially accomplish the same function as the omni-directional lever are cables and pulleys, a solid rod through a gimbal, a solid rod without a gimbal (which would provide less force but greater displacement), or attaching products directly to the central hub 12.

The mounting of the product to the force transfer means 13 is accomplished through a mounting means 15. The terms "mounting" or "fixturing" are broadly defined to include any means for allowing a stimuli to be applied to the product. Therefore, mounting and fixturing do not necessarily require the product to be fastened rigidly in any one given fixed position by a mechanical device of some sort. For example, the product could merely be placed upon a surface and be subjected to vibration or heat stimuli. Mounting means 15 can comprise any number of suitable means or devices such as clamps, bolts, screws, hooks, fasteners, adhesives, straps, glue, welding (metallurgical attachment), intermediate spacer block or fixture, suction (vacuum), electromagnetic, and in some cases in which the other mounting locations are securely mounted, the attachment can be simply being in contact or periodic contact. Preferably, if a product has a number of mounting locations (i.e., an automobile dashboard) it should have an apparatus in accordance with the present invention mounted to each mounting location in order to maximize the benefits of the testing. Alternatively, an apparatus in accordance with the present invention could also be mounted to the product at a non-mounting location.

The force transfer means 13 extends upwardly from the central hub 12 until it passes through a device, such as a gimbal means 16, for allowing the force transfer means 13 to move longitudinally and in all three axes. The gimbal means 16 is mounted to the planar member 3 in proximity to an area defining an aperture 17 located in the planar member 3. In a preferred embodiment, the gimbal means 16 is comprised of an outer race mounted through appropriate means so that it can rotate freely perpendicular to its main centerline; an inner race mounted through bearings to the outer race such that it can rotate freely perpendicular to its main centerline and perpendicular to the outer race's axis of rotation; an inner linear bearing (means for allowing a rod or lever to move linearly through the gimbal means 16) which supports the lever or rod of the force transfer means 13. The purpose of this configuration is to allow the rod or lever attached to the central hub 12 to move freely while restraining the pivot point such that the free end of the rod or lever which will be attached to the product, will move in reaction to all of the motions of the central hub 12. This recreates the motion of the central hub 12 at a location which is free from the proximity of the actuators 5 and can therefore be brought in close proximity to the product to facilitate mounting or attachment. The gimbal means 16 is nominally mounted at the midpoint of the rod sections of the force transfer means 13. In an alternative embodiment, the gimbal means 16 may be adjustable in order to move upwardly or downwardly along the rod sections. This feature would change the moment arm of the force transfer means 13 (e.g., omni-directional lever) so that either more force and less displacement is realized at the mounting location of the product or more displacement and less force is realized at the mounting location of the product. In other words, an adjustable moment is achievable on the force transfer means 13 by varying the position of the gimbal means 16. Once passing through the gimbal means 16, the force transfer means 13 continues to extend upwardly until it terminates at the mounting means 15. The mounting means 15 is shown here securing a workpiece 18, such as a cup. However, many other types of products and components are envisioned to be tested, such as, but not limited to, automotive components, aircraft components, marine components, electronic components (including solid state), consumer products, and construction materials. Also, it is possible for the force transfer means 13 to be placed against the product to be tested, without the need for mounting. For example, the force transfer means 13 can merely abut the product.

Finally, the entire apparatus 1 may also comprise a housing such as a chamber 19, or other suitable structure, that may house one or more apparatuses 1. The chamber 19 is preferably sealable so as to be able to carefully control the introduction and evacuation of stimuli into and out of the chamber 19, as well as controlling the level of stimuli being applied to the product inside the chamber 19.

Figure 2:
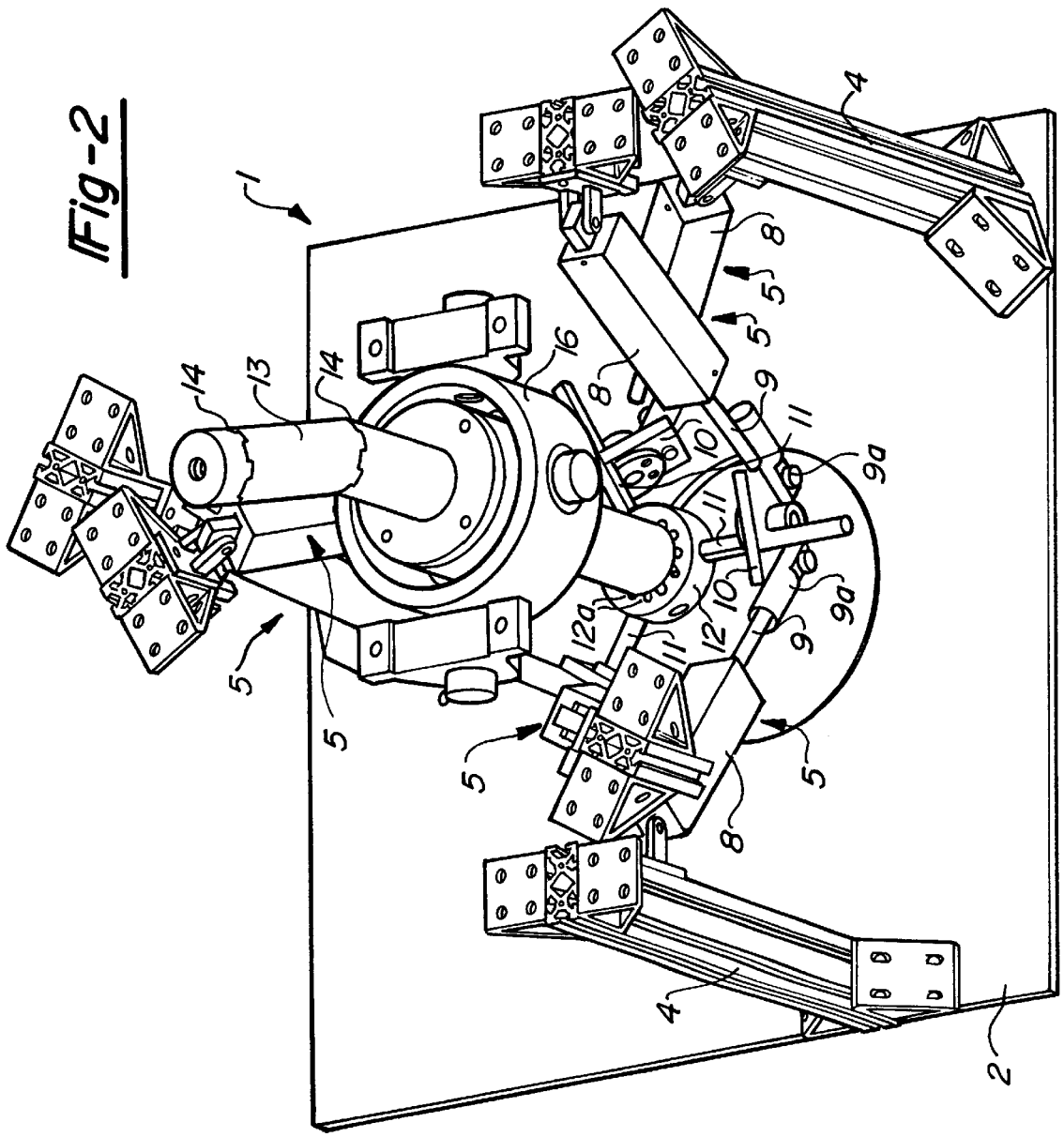
FIG. 2 is an overhead perspective view of a portion of the apparatus shown in FIG. 1, in accordance with one aspect of the present invention.

Referring to FIG. 2, there is shown an overhead perspective view of a portion of the apparatus shown in FIG. 1, in accordance with one aspect of the present invention. In this view, however, the planar member 3 has been removed to allow greater visibility of the various components of the apparatus 1, including the actuators 5, the central hub 12, and the gimbal means 16.

In an alternative embodiment, it is envisioned that a product may be mounted to the central hub 12, thereby eliminating the need for a force transfer means 13, gimbal means 16, and a planar member 3. Referring to FIG. 2, the central hub 12 could be equipped with mounting means 12*a* to secure a product, or alternatively, the product could be mounted directly to the central hub 12 itself. In this sense, the central hub 12 would function as a force transfer means, that is transferring force and torque to the product being tested. Of course, the use of this particular alternative will depend upon the size of the product, the key consideration being that the product should not interfere with the routine operation of the actuators 5.

Although not specifically illustrated in the figures, the apparatus also comprises means for actuating the plurality of force imparting means (e.g., pneumatic actuators), means for subjecting the product to vibration, means for subjecting the product to a temperature, means for subjecting the product to pressure, means for subjecting the product to ultraviolet radiation, means for subjecting the product to chemical exposure, means for subjecting the product to humidity, means for subjecting the product to mechanical cycling, means for subjecting the product to mechanical loading, means for controlling the amount of vibration that the product is subjected to by the apparatus, means for controlling the level of temperature that the product is subjected to by the apparatus, means for controlling the level of pressure that the product is subjected to by the apparatus, means for controlling the level of ultraviolet radiation that the product is subjected to by the apparatus, means for controlling the level of chemical exposure that the product is subjected to by the apparatus, means for controlling the level of humidity that the product is subjected to by the apparatus, means for controlling the amount of mechanical cycling that the product is subjected to by the apparatus, and means for controlling the amount of mechanical loading that the product is subjected to by the apparatus.

The apparatus of the present invention is capable of producing a frequency range from 2 Hz to infinity. However, in practice the damping properties of the joints and materials of the product will limit the upper frequency that can be achieved. Additionally, the apparatus can be placed in any suitable chamber that is preferably capable of producing a thermal range between at least −60 degrees C. to at least 177 degrees C., a controlled temperature ramp rate of at least 5 degrees C./minute and humidity between 5% to 95% relative humidity.

Figure 3:
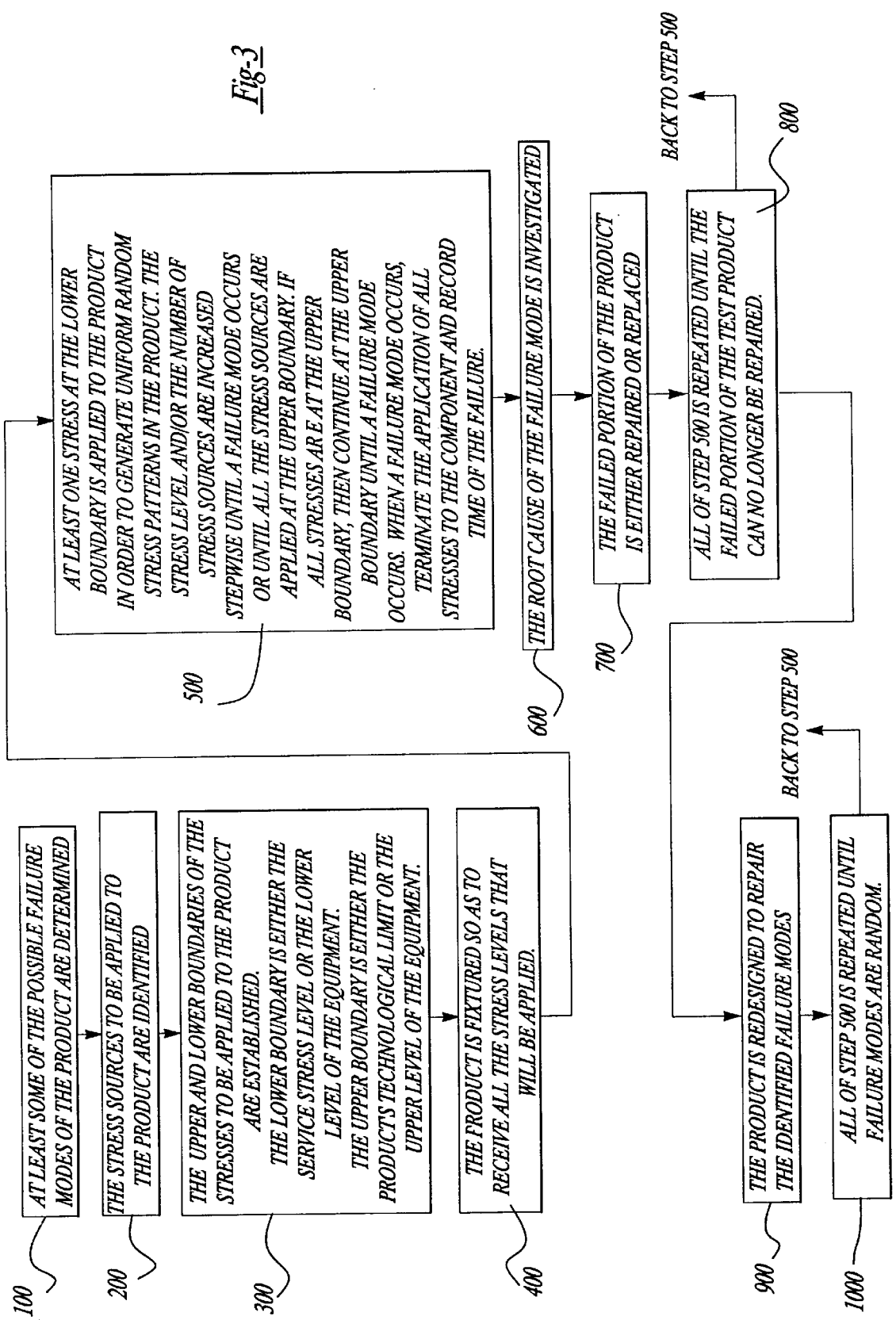
FIG. 3 is a flow chart of a method for testing a product under different conditions, in accordance with one aspect of the present invention.

An example of a method of testing a product under different conditions in order to identify all of its possible failure modes would comprise the following general methodology and is also illustrated in the flow chart depicted in FIG. 3.

Referring to FIG. 3, at step 100, at least some of the possible failure modes of the product are determined. Possible failure modes are generally determined by past experience (e.g., warranty claims, field data, previous testing), computer modeling, production experience, and materials failure analysis. It is noteworthy that not all the failure modes may be identified. Nevertheless, they may ultimately appear as a result of the application of stresses.

Referring to FIG. 3, at step 200, the stress sources to be applied to the product are identified. The possible stress sources to be applied are determined in the same manner as in step 100 in that all failure modes identified in step 100 are used and all stress sources that contribute to those failure modes are listed. However, knowledge of failure modes does not necessarily identify the root cause of an individual root stress. For example, a plastic break may require optical inspection, such as scanning electron microscopy, to determine fracture type before the underlying stress causing the fracture may be determined.

Referring to FIG. 3, at step 300, the upper and lower boundaries of the stresses to be applied to the product are established. The lower stress boundary is either the service stress level or the lower level of the equipment being used. The upper stress boundary is either the product technological limit or the upper level of the equipment being used. The lower stress boundary is determined by: (1) service stress levels for the product which may be determined by past experience, expectations, or computer modeling or (2) the lower controllable level of the equipment, with service stress levels being preferred over the lower controllable level of the equipment. The upper stress boundary is determined by: (1) the product technological limit (which may not be known) which is the destruct limit of the product's constitutive materials; or (2) the lower controllable level of the equipment, with the product technological limit being preferred over the upper controllable level of the equipment.

Referring to FIG. 3, at step 400, the product is fixtured so as to receive all the stress levels and sources that will be applied. For example, humidity will be applied by delivering humid air to the product by placing the product in a chamber available from any number of sources such as Thermatron (Grand Rapids, Mich.). With respect to temperature, there are two basic stress sources: (1) actual temperature and (2) temperature ramp rate. Accordingly, the maximum upper temperature, the minimum lower temperature, and the temperature ramp rate all need to be determined. Dwell time is minimized such that it allows the product to reach the temperature of the chamber. With respect to vibration, preferably each mounting location or point of the product is connected or mounted to an apparatus in accordance with the present invention. The six axis apparatus in accordance with the present invention may either be in the chamber itself or extending through a diaphragm or sleeve into the chamber. With respect to ultraviolet radiation, a device such as carbon arc lamp can be placed in the chamber itself. With respect to chemical exposure or attack, this can be accomplished in several ways. First, the product can be exposed prior to actual testing. Additionally, real time exposure may be achieved by spraying the chemical on the product while in the chamber. The chemical spray may be applied periodically or continuously. It may be important to have the spray dry out. The chemical stress level can be increased by either increasing the chemical spray rate or increasing the concentration of the chemical spray. With respect to mechanical loading, a pneumatic cylinder is used most of the time. However, dead weights and solenoids may also be used. Both the loading as well as the time for each cycle can be varied. Finally, pressure (such as air pressure) can be applied. In each case, there is a need to provide a means to control and adjust the levels of the various stresses.

Referring to FIG. 3, at step 500, the stress application loop begins. Preferably, at least one stress at the lower boundary is applied to the product in order to generate uniform random stress patterns in the product. However, it should be noted that stress may be applied at any point in the continuum ranging from the lower to the upper boundary. The stress level and/or the number of stress sources are increased stepwise until a failure mode occurs or until all the stress sources are applied at the upper boundary. If all stress sources are at the upper boundary, then continue applying the stress sources at the upper boundary until a failure mode occurs. When a failure mode occurs, terminate the application of all stresses to the product, and record the time of the failure mode.

Referring to FIG. 3, at step 600, the root cause of the failure mode is investigated. This investigation or analysis is also referred to as a failure analysis. First, visual inspection is carried out to determine which feature of the product or system has failed. This includes documentation of the failure that may include written records, photographs or videotape. Second, microscopic inspection is performed if a failure feature has been created. Fractology involves: (a) initial failure evaluation of the fracture face to identify the fracture type. The possible fracture types include fatigue, rupture, chemical attack, overload, and torsion/tensile/bending/elongation/distortion. Documentation of the fracture face is produced which may be written records, photographs or sketches. Third, if no failure feature has been created, then the product is inspected to determine whether the assembly was incorrect, the material was incorrect, or if the production was incorrect. This includes documentation that may include written records, photographs or videotape. Fourth, a stress source determination is carried out. At the stress levels at which testing stopped, apply one stress at a time, starting with the one that most likely caused the failure based on the investigation of the failed product. If no single stress source is found to reproduce the failure, apply a combination of stresses. If no combination of stresses recreates the specific failure mode before different failure modes are created, then the failure mode is random and therefore, the design is optimized. If a failure feature was created and can not be thoroughly understood by microscopic inspection, then further failure analysis is required which requires that the product that failed be removed from further testing. Further failure analysis may include: a scanning electron microscope, chemical analysis to determine chemical composition as well as to detect contaminants, infrared spectroscopy to determine chemical composition as well as to detect contaminants, dye penetration to detect cracks, magnetic flux, x-ray, ultrasound, and finite element analysis.

Referring to FIG. 3, at step 700, the failed portion of the product is either repaired or replaced.

Referring to FIG. 3, at step 800, all of step 500 is repeated until the failed portion of the test product can no longer be repaired.

Figure 4:
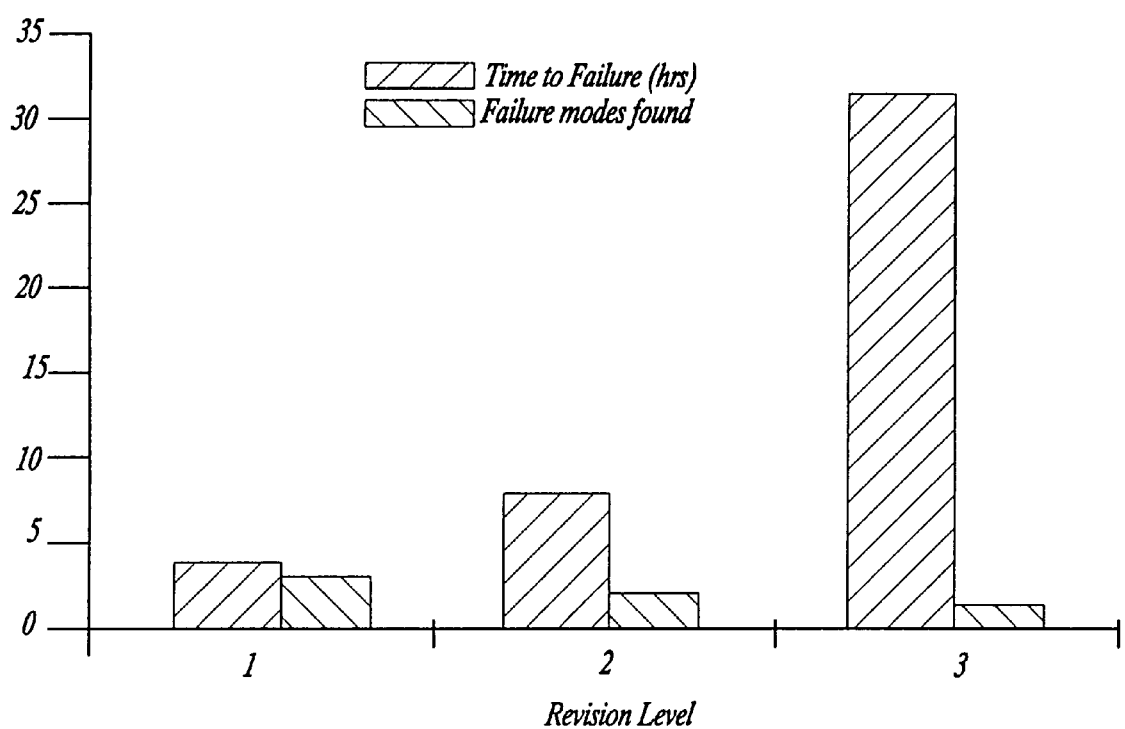
FIG. 4 is a graphical illustration of the results of a method for testing a product under different conditions, in accordance with one aspect of the present invention.

Referring to FIG. 3, at step 900, the product is redesigned to repair the identified failure modes. In doing so, the following are considered: the time to failure, the number of failure modes, and whether the failure modes were repeatable or random. This is one way of determining whether the product design has been optimized (see FIG. 4).

Referring to FIG. 3, at step 1000, all of step 500 is repeated until the failure modes are random. The failure modes are tracked to determine whether they have been corrected. However, this method does not generate a statistical reliability number.

These steps can be repeated or altered to alternatively or simultaneously include various levels of temperature, vibration, pressure, ultraviolet radiation, chemical exposure, humidity, mechanical cycling, and mechanical loading, depending on the product to be tested.

An example of a method of testing a product under different conditions in order to identify all of its possible failure modes, is presented below:

EXAMPLE

An automotive cup holder made of a rigid plastic, having a mechanism for storing and deploying the cup holder receptacles, and two cup holder receptacles is chosen as the product to be tested. As defined in step 100, some of the potential failure modes are identified. These are cracking of plastic at mounting boss, sticking of storing mechanism re-engineering the cup holder useless, and assembly clips cracking due to excessive interference. As defined in step 200, all of the stress sources that can produce damage in the part are identified. These are temperature (hot and cold), temperature ramp rate, cycle rate on the storing mechanism, cycle rate on cup insertion (drop), cup load, storing mechanism load, chemical attack from petroleum lubricant, non-petroleum lubricant beverages (coffee, carbonated soda), UV light, and forces at mounting locations (three translations, 3 rotations). As defined in step 300, the upper and lower boundaries of each stress source is established. These are −40 degrees C. to 177 degrees C., a temperature ramp rate of 15 degrees C./minute, 1 storing mechanism/minute to 10 storing mechanism/minute, 1 cup drop/minute to 10 cup drops/minute, ½ lb to 50 lb. cup load, ¼ lb. to 15 lbs. storing mechanism load, no petroleum lubricant to lubricated with SÆ 20, no non-petroleum lubricant to lubricated with lithium grease, no beverage to 12 oz. of coffee (regular) poured over component or 12 oz. of cola (regular) poured over component, UV light from one 200 watt UV lamp, 10 lb. peak force and 10 in.-lb. peak torque at each of four mounting locations to 100 lb. peak force and 100 in.-lb. peak torque at each of four mounting locations. As defined in step 400, the four mounting locations are each bolted to one six-axis actuator apparatus, in accordance with the present invention. A pneumatic cylinder is positioned to apply the load to the storing mechanism. Two pneumatic cylinders are fitted with mock cups and positioned to apply load to the cup holder receptacles when they are in the open position. The setup is placed in a chamber with heating and cooling controls. Controls are placed on the pneumatic cylinders to create the desired cycle rates. A UV lamp is placed in the chamber. Samples of the lubricants and beverages are prepared. As defined in step 500, the temperature cycle is applied by cycling the temperature from room temperature to 177 degrees C., to −40 degrees C. and back to room temperature. This applies three of the stress stimuli to the product. Then while continuing to apply the thermal cycle, the mounting location energy is applied at all four mounting location at the lowest energy setting listed above. This stress condition is continued for one thermal cycle. While all of the above stimuli are applied at present levels, the mechanical cycling is started with loads and rates at the lowest setting listed above. This stress condition is continued for one thermal cycle. All of the mechanical loading (cycling and mounting points) are raised ¼ of the way to full load. This stress condition is continued for one thermal cycle. All of the mechanical loading (cycling and mounting points) are raised an additional ¼ of the way to full load. This stress condition is continued for one thermal cycle. All of the mechanical loading (cycling and mounting points) are raised an additional ¼ of the way to full load. This stress condition is continued for one thermal cycle. At this point with ¾ of the mechanical loading applied, the first failure mode occurs. This triggers step 600. The initial visual inspection indicates that a plastic tab in the storing mechanism latch has cracked. Optical inspection reveals that the crack originated due to a flaw (cavity) that then fatigued under loading. No further inspection is needed. The crack is documented and repaired (step 700). Step 500 is continued with full mechanical loading for one thermal cycle. The UV light is turned on with all other stress sources at previous levels and another thermal cycle is conducted. A second failure mode occurs. This triggers step 600 for the second time. The initial visual inspection indicates that the edge of one of the cup holder receptacles had cracked. Optical inspection indicates that the lip of the receptacle fatigued. The part on the component is replaced and the mechanical loading of the cup insertion only is applied at previous levels (one stress source) to verify which stress source caused the failure. This stress source does not re-create the failure. The mechanical loading of the cup insertion and the mounting locations is applied at previous levels (two stress source combination) and the failure mode is reproduced. The conclusion is that the mounting location force randomly moves the cup holder so the lip of the cup holder is struck by the simulated cup as it is being inserted. The failure mode is documented and the component is fixed (step 700). At this point all stress sources are at the maximum level. Thermal cycles are continued with all stress levels at there previous levels until a failure occurs. A failure occurs after 6 additional thermal cycles. This triggers step 600 for the third time. The initial visual inspection indicates that the hinge of the storing mechanism has worked out of its seat. Optical inspection reveals that there is no failure feature, the parts have simply become separated. Stepping in the stress at the previous levels determines that the mechanical loading of the storing mechanism at higher temperatures (when the plastic was most elastic) caused the hinge to work out of its seat. Step 500 is continued, but no other failure modes can be generated. The third failure mode continues to repeat. Step 900 is conducted to redesign the failed areas. The correction steps are noted and the time to failure and failure modes are complied thereof. Step 500 (per step 1000) is repeated. Stresses are added in and raised to maximum levels without failure. Failure finally occurs after 10 thermal cycles at maximum stress (note that this is a significant increase in time to failure). Step 600 reveals that the failure is a crack in the middle of the bottom of the left cut holder. Efforts to reproduce this failure are unsuccessful, in the process two other failure modes occurs which can not be reproduced. Random failure modes had been achieved. The part appears to be optimized.

The foregoing description is considered illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

What is claimed is:

1. An apparatus for applying a force to a product, comprising:
    a force imparting member, said force imparting member being capable of creating six axis uniform random stresses in the product;
    a force transfer member for transferring the force from said force imparting member to the product, said force transfer member being fastened to said force imparting member, said force transfer member having a mounting member for mounting to the product; and
    a member for allowing said force transfer member to move longitudinally and in all three axes.

2. An apparatus in accordance with claim 1, further comprising:
    a base;
    a support member, said support member having a first end and a second end, said first end of said support member being fastened to said base, said force imparting member being fastened to said support member;
    an actuator for actuating said force imparting member; and
    a planar member, said second ends of said support member being fastened to said planar member, said planar member having an area defining an aperture, said force transfer member extending through the aperture of said planar member, said force transfer member having a plurality of integral hinge elements to allow said force transfer member to be angularly positioned.

3. An apparatus in accordance with claim 1, further comprising:
    a device for subjecting the product to vibration;
    a device for subjecting the product to a temperature;
    a device for subjecting the product to pressure;
    a device for subjecting the product to ultraviolet radiation;
    a device for subjecting the product to chemical exposure;
    a device for subjecting the product to humidity;
    a device for subjecting the product to mechanical cycling; and
    a device for subjecting the product to mechanical loading.

4. An apparatus in accordance with claim 3, further comprising:
    a device for controlling the amount of vibration that the product is subjected to by the apparatus;
    a device for controlling the level of temperature that the product is subjected to by the apparatus;
    a device for controlling the level of pressure that the product is subjected to by the apparatus;
    a device for controlling the level of ultraviolet radiation that the product is subjected to by the apparatus;
    a device for controlling the level of chemical exposure that the product is subjected to by the apparatus;
    a device for controlling the level of humidity that the product is subjected to by the apparatus;
    a device for controlling the amount of mechanical cycling that the product is subjected to by the apparatus; and
    a device for controlling the amount of mechanical loading that the product is subjected to by the apparatus.

5. An apparatus in accordance with claim 1, wherein said force imparting member comprises a plurality of actuators, said plurality of actuators operating at different frequencies with respect to one another, wherein the difference in frequencies of said plurality of actuators creates a six axis uniform random stress in the product, said plurality of actuators being capable of producing a frequency in the range of about 2 Hz to about infinity.

6. An apparatus for applying a force to a product, comprising:
    a plurality of actuators, said actuators being capable of creating six axis uniform random stresses in the product;
    a force transfer member, said force transfer member transferring the force from said actuators to the product, said force transfer member being fastened to said actuators, said force transfer member having a mounting member for mounting to the product, said force transfer member having an adjustable moment; and
    a gimbal for allowing said force transfer member to move longitudinally and in all three axes.

7. An apparatus in accordance with claim 6, further comprising:
    a base;
    support members, said support members having a first end and a second end, said first end of said support members being fastened to said base, said actuators being fastened to said support member;
    an actuator for actuating said actuators; and
    a planar member, said support members being fastened to said planar member, said planar member having an area defining an aperture, said force transfer member extending through the aperture of said planar member, said force transfer member having a plurality of integral hinge elements to allow said force transfer member to be angularly positioned.

8. An apparatus in accordance with claim 6, further comprising:
    a device for subjecting the product to vibration;
    a device for subjecting the product to a temperature;
    a device for subjecting the product to pressure;
    a device for subjecting the product to ultraviolet radiation;
    a device for subjecting the product to chemical exposure;
    a device for subjecting the product to humidity;
    a device for subjecting the product to mechanical cycling; and a device for subjecting the product to mechanical loading.

9. An apparatus in accordance with claim 8, further comprising:
- a device for controlling the amount of vibration that the product is subjected to by the apparatus;
- a device for controlling the level of temperature that the product is subjected to by the apparatus;
- a device for controlling the level of pressure that the product is subjected to by the apparatus;
- a device for controlling the level of ultraviolet radiation that the product is subjected to by the apparatus;
- a device for controlling the level of chemical exposure that the product is subjected to by the apparatus;
- a device for controlling the level of humidity that the product is subjected to by the apparatus;
- a device for controlling the amount of mechanical cycling that the product is subjected to by the apparatus; and
- a device for controlling the amount of mechanical loading that the product is subjected to by the apparatus.

10. A method for optimizing the design of a product, comprising the steps of:
- a) providing a product;
- b) mounting the product to a force transfer member; and
- c) applying at least one stimuli to the product, wherein the application of the at least one stimuli is capable of creating six axis random uniform stresses in the product, wherein the at least one stimuli is selected from the group consisting of vibration, temperature, pressure, ultraviolet radiation, chemical exposure, humidity, mechanical cycling, mechanical loading, and combinations thereof.

11. A product produced in accordance with claim 10.

12. A method in accordance with claim 10, further comprising the step of: d) continuing to apply the at least one stimuli until at least one failure mode is encountered.

13. A method in accordance with claim 12, further comprising the step of: e) repairing the failed product.

14. A method in accordance with claim 13, further comprising the step of: f) repeating steps b), c), d), and e) until a second failure mode is encountered.

15. A method in accordance with claim 14, further comprising the step of: g) redesigning the product.

16. A method in accordance with claim 15, further comprising the step of: h) repeating steps b), c), d), e), f), and g) until any failure modes encountered are random.

17. A method in accordance with claim 12, further comprising the step of: e) replacing the failed product.

18. A method in accordance with claim 17, further comprising the step of: f) repeating steps b), c), d), and e) until a second failure mode is encountered.

19. A method in accordance with claim 18, further comprising the step of: g) redesigning the product.

20. A method in accordance with claim 19, further comprising the step of: h) repeating steps b), c), d), e), f), and g) until any failure modes encountered are random.

21. A method for applying a stimuli to a product, comprising the steps of:
- a) providing a product;
- b) mounting the product to a force transfer member;
- c) applying a first stimuli to the product, wherein the first stimuli is selected from the group consisting of vibration, temperature, pressure, ultraviolet radiation, chemical exposure, humidity, mechanical cycling, mechanical loading, and combinations thereof; and
- d) simultaneously applying at least one other stimuli to the product, wherein the at least one other stimuli is selected from the group consisting of vibration, temperature, pressure, ultraviolet radiation, chemical exposure, humidity, mechanical cycling, mechanical loading, and combinations thereof;

wherein the application of the first or the at least one other stimuli is capable of creating six axis random uniform stresses in the product.

22. A product produced in accordance with claim 21.

23. A method in accordance with claim 21, further comprising the step of: e) continuing to apply the first and, optionally, the at least one other stimuli until at least one failure mode is encountered.

24. A method in accordance with claim 23, further comprising the step of: f) repairing the failed product.

25. A method in accordance with claim 24, further comprising the step of: g) repeating steps c), d), e), and f) until a second failure mode is encountered.

26. A method in accordance with claim 25, further comprising the step of: h) redesigning the product.

27. A method in accordance with claim 26, further comprising the step of: i) repeating steps c), d), e), f), g), and h) until any failure modes encountered are random.

28. A method in accordance with claim 23, further comprising the step of: f) replacing the failed product.

29. A method in accordance with claim 28, further comprising the step of: g) repeating steps c), d), e), and f) until a second failure mode is encountered.

30. A method in accordance with claim 29, further comprising the step of: h) redesigning the product.

31. A method in accordance with claim 30, further comprising the step of: i) repeating steps c), d), e), f), g), and h) until any failure modes encountered are random.

32. A method for applying a stimuli to a product, comprising the steps of:
- a) providing a product;
- b) mounting the product to a force transfer member; and
- c) applying at least one stimuli to the product, wherein the application of the at least one stimuli is capable of creating six axis random uniform stresses in the product, wherein the level of stimuli is increased over time, wherein the at least one stimuli is selected from the group consisting of vibration, temperature, pressure, ultraviolet radiation, chemical exposure, humidity, and combinations thereof.

33. A product produced in accordance with claim 32.

34. A method in accordance with claim 32, further comprising the step of: d) continuing to apply the at least one stimuli until at least one failure mode is encountered.

35. A method in accordance with claim 34, further comprising the step of: e) repairing the failed product.

36. A method in accordance with claim 35, further comprising the step of f) repeating steps b), c), d), and e) until a second failure mode is encountered.

37. A method in accordance with claim 36, further comprising the step of: g) redesigning the product.

38. A method in accordance with claim 37, further comprising the step of: h) repeating steps b), c), d), e), f), and g) until any failure modes encountered are random.

39. A method in accordance with claim 34, further comprising the step of: e) replacing the failed product.

40. A method in accordance with claim 39, further comprising the step of: f) repeating steps b), c), d), and e) until a second failure mode is encountered.

41. A method in accordance with claim 40, further comprising the step of: g) redesigning the product.

42. A method in accordance with claim 41, further comprising the step of: h) repeating steps b), c), d), e), f), and g) until any failure modes encountered are random.

43. A method for applying a stimuli to a product, comprising the steps of:
   a) providing a product;
   b) mounting the product to a force transfer member;
   c) applying a first stimuli, wherein the level of stimuli is increased over time, wherein the first stimuli is selected from the group consisting of vibration, temperature, pressure, ultraviolet radiation, chemical exposure, humidity, mechanical cycling, mechanical loading, and combinations thereof; and
   d) simultaneously applying at least one other stimuli to the product, wherein the level of stimuli is increased over time, wherein the at least one other stimuli is selected from the group consisting of vibration, temperature, pressure, ultraviolet radiation, chemical exposure, humidity, mechanical cycling, mechanical loading, and combinations thereof;
      wherein the application of the first or the at least one other stimuli is capable of creating six axis random uniform stresses in the product.

44. A product produced in accordance with claim 43.

45. A method in accordance with claim 43, further comprising the step of: e) continuing to apply the first and, optionally, the at least one other stimuli until at least one failure mode is encountered.

46. A method in accordance with claim 45, further comprising the step of: f) repairing the failed product.

47. A method in accordance with claim 46, further comprising the step of: g) repeating steps c), d), e), and f) until a second failure mode is encountered.

48. A method in accordance with claim 47, further comprising the step of: h) redesigning the product.

49. A method in accordance with claim 48, further comprising the step of: i) repeating steps c), d), e), f), g), and h) until any of the failure modes encountered are random.

50. A method in accordance with claim 45, further comprising the step of: f) replacing the failed product.

51. A method in accordance with claim 50, further comprising the step of: g) repeating steps c), d), e), and f) until a second failure mode is encountered.

52. A method in accordance with claim 51, further comprising the step of: h) redesigning the product.

53. A method in accordance with claim 52, further comprising the step of: i) repeating steps c), d), e), f, g), and h) until any of the failure modes encountered are random.

54. A method for applying a stimuli to a product, comprising the steps of:
   a) determining the service loads of stimuli that are applied to the product during routine operation, wherein the stimuli is selected from the group consisting of temperature, vibration, pressure, ultraviolet radiation, chemical exposure, humidity, mechanical cycling, mechanical loading, and combinations thereof;
   b) applying at least one stimuli at levels exceeding the service loads of stimuli that are applied to the product during routine operation, wherein the application of the at least one stimuli is capable of creating six axis random uniform stresses in the product; and
   c) continuing to apply the at least one stimuli until at least one failure mode is encountered.

55. A method in accordance with claim 54, wherein the stimuli is increased over time.

56. A product produced in accordance with claim 54.

57. A method in accordance with claim 54, further comprising the step of: d) repairing the failed product.

58. A method in accordance with claim 57, further comprising the step of: e) repeating steps b), c), and d) until a second failure mode is encountered.

59. A method in accordance with claim 58, further comprising the step of: f) redesigning the product.

60. A method in accordance with claim 59, further comprising the step of: g) repeating steps b), c), d), e), and f) until any of the failure modes encountered are random.

61. A method in accordance with claim 54, further comprising the step of: d) replacing the failed product.

62. A method in accordance with claim 61, further comprising the step of: e) repeating steps b), c), and d) until a second failure mode is encountered.

63. A method in accordance with claim 62, further comprising the step of: f) redesigning the product.

64. A method in accordance with claim 63, further comprising the step of: g) repeating steps b), c), d), e), and f) until any of the failure modes encountered are random.

65. A method for applying a stimuli to a product, comprising the steps of:
   a) determining the service loads of stimuli that are applied to the product during routine operation, wherein the stimuli is selected from the group consisting of temperature, vibration, pressure, ultraviolet radiation, chemical exposure, humidity, mechanical cycling, mechanical loading, and combinations thereof;
   b) fixturing the product to a member for applying stimuli;
   c) applying at least one stimuli at levels exceeding the service loads of stimuli that are applied to the product during routine operation, wherein the application of the at least one stimuli is capable of creating six axis random uniform stresses in the product; and
   d) continuing to apply the at least one stimuli until at least one failure mode is encountered.

66. A method in accordance with claim 65, wherein the stimuli is increased over time.

67. A product produced in accordance with claim 65.

68. A method in accordance with claim 65, further comprising the step of: e) repairing the failed product.

69. A method in accordance with claim 68, further comprising the step of: f) repeating steps c), d), and e) until a second failure mode is encountered.

70. A method in accordance with claim 69, further comprising the step of: g) redesigning the product.

71. A method in accordance with claim 70, further comprising the step of: h) repeating steps c), d), e), f), and g) until any of the failure modes encountered are random.

72. A method in accordance with claim 65, further comprising the step of: e) replacing the failed product.

73. A method in accordance with claim 72, further comprising the step of: f) repeating steps c), d), and e) until a second failure mode is encountered.

74. A method in accordance with claim 73, further comprising the step of: g) redesigning the product.

75. A method in accordance with claim 74, further comprising the step of: h) repeating steps c), d), e), f), and g) until any of the failure modes encountered are random.

76. A method for applying a stimuli to a product, comprising the steps of:
   a) determining the service loads of stimuli that are applied to the product during routine operation, wherein the stimuli is selected from the group consisting of temperature, vibration, pressure, ultraviolet radiation, chemical exposure, humidity, mechanical cycling, mechanical loading, and combinations thereof;
   b) applying at least one stimuli at levels exceeding the service loads of stimuli that are applied to the product during routine operation, wherein the application of the at least one stimuli is capable of creating six axis random uniform stresses in the product;

c) continuing to apply the at least one stimuli until a first failure mode is encountered;

d) repairing the failed product; and e) repeating steps b), c), and d) until a second failure mode of the product is encountered.

77. A method in accordance with claim 76, wherein the stimuli is increased over time.

78. A product produced in accordance with claim 76.

79. A method in accordance with claim 76, wherein in step d) the failed product is replaced instead of repaired.

80. A method in accordance with claim 79, wherein the stimuli is increased over time.

81. A product produced in accordance with claim 79.

82. A method in accordance with claim 76, further comprising the step of: f) repeating steps b, c), d), and e) until any of the failure modes encountered are random.

83. A method for applying a stimuli to a product, comprising the steps of:

a) determining the service loads of stimuli that are applied to the product during routine operation, wherein the stimuli is selected from the group consisting of temperature, vibration, pressure, ultraviolet radiation, chemical exposure, humidity, mechanical cycling, mechanical loading, and combinations thereof;

b) fixturing the product to a member for applying stimuli;

c) applying at least one stimuli at levels exceeding the service loads of stimuli that are applied to the product during routine operation, wherein the application of the at least one stimuli is capable of creating six axis random uniform stresses in the product;

d) continuing to apply the at least one stimuli until a first failure mode is encountered;

e) repairing the failed product; and f) repeating steps c), d) and e) until a second failure mode of the product is encountered.

84. A method in accordance with claim 83, wherein the stimuli is increased over time.

85. A product produced in accordance with claim 83.

86. A method in accordance with claim 83, wherein in step e) the failed product is replaced instead of repaired.

87. A method in accordance with claim 86, wherein the stimuli is increased over time.

88. A product produced in accordance with claim 86.

89. A method in accordance with claim 83, further comprising the step of: g) repeating steps c), d), e), and f) until any of the failure modes encountered are random.

90. A method for applying a stimuli to a product, comprising the steps of:

a) determining the service loads of stimuli that are applied to the product during routine operation, wherein the stimuli is selected from the group consisting of temperature, vibration, pressure, ultraviolet radiation, chemical exposure, humidity, mechanical cycling, mechanical loading, and combinations thereof;

b) applying at least one stimuli at levels exceeding the service loads of stimuli that are applied to the product during routine operation, wherein the application of the at least one stimuli is capable of creating six axis random uniform stresses in the product;

c) continuing to apply the at least one stimuli until at least one failure mode is encountered; and d) conducting an analysis of the failure mode.

91. A method in accordance with claim 90, wherein the stimuli is increased over time.

92. A product produced in accordance with claim 90.

93. A method in accordance with claim 90, further comprising the step of: e) repairing the failed product.

94. A method in accordance with claim 90, further comprising the step of: e) replacing the failed product.

95. A method in accordance with claim 94, further comprising the step of: f) repeating steps b), c), d), and e) until a second failure mode is encountered.

96. A method in accordance with claim 95, further comprising the step of: g) redesigning the product.

97. A method in accordance with claim 96, further comprising the step of: h) repeating steps b), c), d), e), f), and g) until any of the failure modes encountered are random.

98. A method for applying a stimuli to a product, comprising the steps of:

a) determining the service loads of stimuli that are applied to the product during routine operation, wherein the stimuli is selected from the group consisting of temperature, vibration, pressure, ultraviolet radiation, chemical exposure, humidity, mechanical cycling, mechanical loading, and combinations thereof;

b) fixturing the product to a member for applying stimuli;

c) applying at least one stimuli at levels exceeding the service loads of stimuli that are applied to the product during routine operation, wherein the application of the at least one stimuli is capable of creating six axis random uniform stresses in the product;

d) continuing to apply the at least one stimuli until at least one failure mode is encountered; and e) conducting an analysis of the failure mode.

99. A method in accordance with claim 98, wherein the stimuli is increased over time.

100. A product produced in accordance with claim 98.

101. A method in accordance with claim 93, further comprising the step of: f) repeating steps b), c), d), and e) until a second failure mode is encountered.

102. A method in accordance with claim 101, further comprising the step of: g) redesigning the product.

103. A method in accordance with claim 102, further comprising the step of: h) repeating steps b), c), d), e), f), and g) until any of the failure modes encountered are random.

104. A method in accordance with claim 98, further comprising the step of: f) repairing the failed product.

105. A method in accordance with claim 104, further comprising the step of: g) repeating steps c), d), e), and f) until a second failure mode is encountered.

106. A method in accordance with claim 105, further comprising the step of: h) redesigning the product.

107. A method in accordance with claim 106, further comprising the step of: i) repeating steps c), d), e), f), g), and h) until any of the failure modes encountered are random.

108. A method in accordance with claim 98, further comprising the step of: f) replacing the failed product.

109. A method in accordance with claim 108, further comprising the step of: g) repeating steps c), d), e), and f) until a second failure mode is encountered.

110. A method in accordance with claim 109, further comprising the step of: h) redesigning the product.

111. A method in accordance with claim 110, further comprising the step of: i) repeating steps c), d), e), f), g), and h) until any of the failure modes encountered are random.

112. A method for applying a stimuli to a product, comprising the steps of:

a) determining the service loads of stimuli that are applied to the product during routine operation, wherein the stimuli is selected from the group consisting of temperature, vibration, pressure, ultraviolet radiation, chemical exposure, humidity, mechanical cycling, mechanical loading, and combinations thereof;

b) applying at least one stimuli at levels exceeding the service loads of stimuli that are applied to the product during routine operation, wherein the application of the at least one stimuli is capable of creating six axis random uniform stresses in the product;

c) continuing to apply the at least one stimuli until a first failure mode is encountered;

d) conducting an analysis of the failure mode;

e) repairing the failed product; and f) repeating steps b), c), d), and e) until a second failure mode of the product is encountered and analyzed.

113. A method in accordance with claim 112, wherein the stimuli is increased over time.

114. A product produced in accordance with claim 112.

115. A method in accordance with claim 112, wherein in step e) the failed product is replaced instead of repaired.

116. A method in accordance with claim 115, wherein the stimuli is increased over time.

117. A product produced in accordance with claim 115.

118. A method in accordance with claim 112, further comprising the step of: g) repeating steps b), c), d), e), and f) until any of the failure modes encountered are random.

119. A method for applying a stimuli to a product, comprising the steps of:

a) determining the service loads of stimuli that are applied to the product during routine operation, wherein the stimuli is selected from the group consisting of temperature, vibration, pressure, ultraviolet radiation, chemical exposure, humidity, mechanical cycling, mechanical loading, and combinations thereof;

b) fixturing the product to a member for applying stimuli;

c) applying at least one stimuli at levels exceeding the service loads of stimuli that are applied to the product during routine operation, wherein the application of the at least one stimuli is capable of creating six axis random uniform stresses in the product;

d) continuing to apply the at least one stimuli until a first failure mode is encountered;

e) conducting an analysis of the failure mode;

f) repairing the failed product; and g) repeating steps c), d), e), and f) until a second failure mode of the product is encountered and analyzed.

120. A method in accordance with claim 119, wherein the stimuli is increased over time.

121. A product produced in accordance with claim 119.

122. A method in accordance with claim 119, wherein in step f) the failed product is replaced instead of repaired.

123. A method in accordance with claim 122, wherein the stimuli is increased over time.

124. A product produced in accordance with claim 122.

125. A method in accordance with claim 119, further comprising the step of: h) repeating steps c), d), e), f), and g) until any of the failure modes encountered are random.

* * * * *